United States Patent
Medrano Rupérez et al.

(10) Patent No.: US 8,183,370 B2
(45) Date of Patent: May 22, 2012

(54) PROCESS FOR THE PREPARATION OF ABACAVIR

(75) Inventors: Jorge Medrano Rupérez, Barcelona (ES); Julio Campon Pardo, Barcelona (ES); Laia Elías Rius, Barcelona (ES); Ramón Berenguer Maimó, Barcelona (ES)

(73) Assignee: Esteve Quimica, SA, Barcelona (ES)

( * ) Notice: Subject to any disclaimer, the term of this patent is extended or adjusted under 35 U.S.C. 154(b) by 424 days.

(21) Appl. No.: 12/443,378

(22) PCT Filed: Sep. 27, 2007

(86) PCT No.: PCT/EP2007/060249
§ 371 (c)(1),
(2), (4) Date: Mar. 27, 2009

(87) PCT Pub. No.: WO2008/037760
PCT Pub. Date: Apr. 3, 2008

(65) Prior Publication Data
US 2010/0004446 A1    Jan. 7, 2010

Related U.S. Application Data

(60) Provisional application No. 60/847,979, filed on Sep. 28, 2006.

(30) Foreign Application Priority Data

Sep. 28, 2006   (EP) .................................. 06121459

(51) Int. Cl.
*C07D 473/16*    (2006.01)
(52) U.S. Cl. ...................................... 544/277
(58) Field of Classification Search ............. 544/277
See application file for complete search history.

(56) References Cited

U.S. PATENT DOCUMENTS

2010/0041883 A1* 2/2010 Medrano Ruperez et al. ................. 544/277

FOREIGN PATENT DOCUMENTS

| EP | 0434450 A2 | 6/1991 |
|----|------------|--------|
| WO | WO9852949 A1 | 11/1998 |
| WO | WO2004089952 A1 | 10/2004 |

OTHER PUBLICATIONS

Torii, Tetrahedron (c), 62(24), 5709-5716.*
Fujiwara, Bioorganic & Medicinal Chemistry Letters (2001), 11(16), 2221-2223.*
Torii, Tetrahedron 62 (2006) 5709-5716.*
Notification of Transmittal of the International Search Report and the Written Opinion of the International Searching Authority, or the Declaration, Mar. 14, 2008, European Patent Office.
Koster, Hubert et al., N-Acyl Protecting Groups for Deoxynucleosides: A Quantitative and Comparative Study, Tetrahedron, 1981 (the year of publication is sufficiently earlier than the effective U.S. filing date and any foreign priority date), pp. 363-369, vol. 37, Issue 2, Elsevier Science Publishers, Amsterdam.

* cited by examiner

*Primary Examiner* — Mark Berch
(74) *Attorney, Agent, or Firm* — Peter B. Scull; Hamilton, DeSanctis & Cha, LLP

(57) ABSTRACT

Process for removal of the amino protective group of a N-acylated {(1S,4R)-4-[2-amino-6-(cyclopropylamino)-9H-purin-9-yl]-cyclopent-2-enyl}methanol of formula (II) where R═H or a ($C_1$-$C_4$)-alkyl, using an inorganic base in a mixture of water and alcohol, to yield abacavir or its salts. The process proceeds very fast and the product can be obtained in high yield and purity.

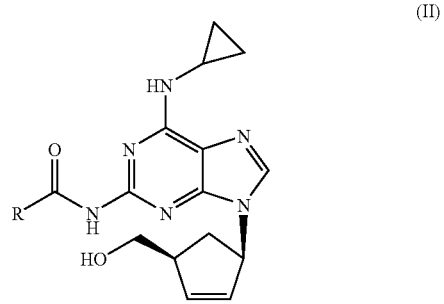

(II)

19 Claims, No Drawings

PROCESS FOR THE PREPARATION OF ABACAVIR

CROSS-REFERENCE TO RELATED APPLICATIONS

The present application is the US national stage application of the Patent Cooperation Treaty (PCT) Application Number PCT/EP2007/060249, filed 27 Sep. 2007, entitled "PROCESS FOR THE PREPARATION OF ABACAVIR"; which designated the United States of America, inter alia; and which claims priority from the European Patent Application, Number 06121459.9, filed 28 Sep. 2006, and from the U.S. Provisional Patent Application, No. 60/847,979, also filed 28 Sep. 2006, the subject matter of each of which hereby being specifically incorporated herein by reference for all that they disclose and teach.

The invention refers to a process for the preparation of an active pharmaceutical ingredient known as abacavir. The process is based on the removal of the protective group of N-2-acyl abacavir using specific basic conditions.

BACKGROUND ART

Abacavir, is the International Nonproprietary Name (INN) of {(1S,4R)-4-[2-amino-6-(cyclopropylamino)-9H-purin-9-yl]-cyclopent-2-enyl}methanol, and CAS No. 136470-78-5. Abacavir sulfate is a potent selective inhibitor of HIV-1 and HIV-2, and can be used in the treatment of human immunodeficiency virus (HIV) infection.

The structure of abacavir hemisulfate salt corresponds to formula (I):

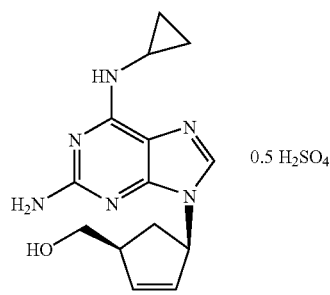

(I)

EP 434450-A discloses certain 9-substituted-2-aminopurines including abacavir and its salts, methods for their preparation, and pharmaceutical compositions using these compounds.

Different preparation processes of abacavir are known in the art. In some of them abacavir is obtained starting from an appropriate pyrimidine compound, coupling it with a sugar analogue residue, followed by a cyclisation to form the imidazole ring and a final introduction of the cyclopropylamino group at the 6 position of the purine ring. Pyrimidine compounds which have been identified as being useful as intermediates of said preparation processes include N-2-acylated abacavir intermediates such as N-{6-(cyclopropylamino)-9-[(1R,4S)-4-(hydroxymethyl)cyclopent-2-enyl]-9H-purin-2-yl}acetamide or N-{6-(cyclopropylamino)-9-[(1R,4S)-4-(hydroxymethyl)cyclopent-2-enyl]-9H-purin-2-yl}isobutyramide. The removal of the amino protective group of these compounds using acidic conditions is known in the art. According to Example 28 of EP 434450-A, the amino protective group of the N-{6-(cyclopropylamino)-9-[(1R,4S)-4-(hydroxymethyl)cyclopent-2-enyl]-9H-purin-2-yl}isobutyramide is removed by stirring with 1N hydrochloric acid for 2 days at room temperature. The abacavir base, after adjusting the pH to 7.0 and evaporation of the solvent, is finally isolated by trituration and chromatography. Then, it is transformed by reaction with an acid to the corresponding salt of abacavir. The main disadvantages of this method are: (i) the use of a strongly corrosive mineral acid to remove the amino protective group; (ii) the need of a high dilution rate; (iii) a long reaction time to complete the reaction; (iv) the need of isolating the free abacavir; and (v) a complicated chromatographic purification process.

Thus, despite the teaching of this prior art document, the research of new deprotection processes of a N-acylated {(1S,4R)-4-[2-amino-6-(cyclopropylamino)-9H-purin-9-yl]-cyclopent-2-enyl}methanol is still an active field, since the industrial exploitation of the known process is difficult, as it has pointed out above. Thus, the provision of a new process for the removal of the amino protective group of a N-acylated {(1S,4R)-4-[2-amino-6-(cyclopropylamino)-9H-purin-9-yl]-cyclopent-2-enyl}methanol is desirable.

SUMMARY OF THE INVENTION

Inventors have found that the removal of the amino protective group of a N-2-acylated {(1S,4R)-4-[2-amino-6-(cyclopropylamino)-9H-purin-9-yl]-cyclopent-2-enyl}methanol using a base in a mixture of water and alcohol proceeds very fast and the product can be obtained in a high yield and with a high purity since there is no significance formation of by-products compared with the method known in the art.

Thus, the present invention refers to the provison of a process for the preparation of abacavir of formula (I), or pharmaceutically acceptable salts thereof, or solvates thereof, comprising reacting a compound of formula (II) with an inorganic base in a mixture of ($C_1$-$C_6$)-alcohol and water, where R is H or a ($C_1$-$C_4$)-alkyl radical.

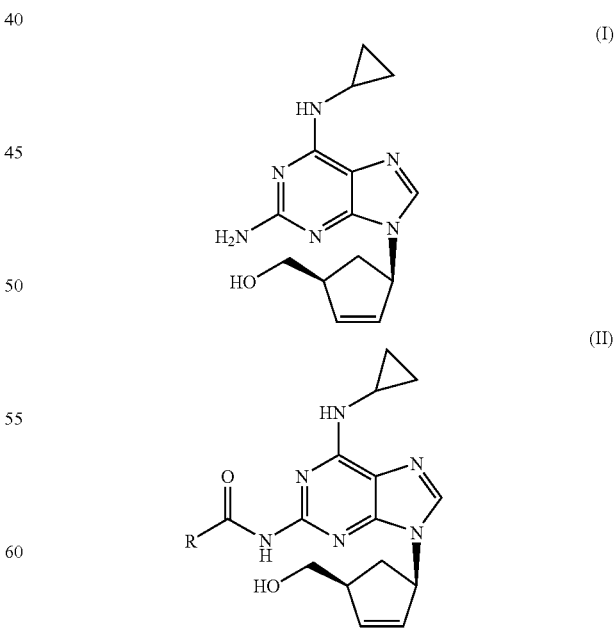

Among the striking advantageous features of the process of the present invention, the following can be mentioned: (i) the hydrolysis carried out in said basic conditions is more efficient; (ii) shorter reaction times are required, since the reaction conditions of the process of the invention allow to perform the hydrolysis at higher temperatures; (iii) lower formation of impurities; in the reaction conditions of the present invention the hydrolysis takes place with a low formation of by-products even at high temperatures, on the contrary, when acidic conditions are used, a fast degradation of the product is observed upon warming; (iv) the reaction volumes are optimized given that the hydrolysis can be carried out at high concentrations; (vi) it takes place without racemization; (vii) the abacavir or its salts are easyly isolated and purified; and (vii) high yields are obtained.

DETAILED DESCRIPTION OF THE INVENTION

As described above, abacavir can be obtained by hydrolysis in basic conditions from compound of formula (II) using an inorganic base. In preferred embodiments compounds of formula (II) are those where R is H, methyl or isopropyl. In a more preferred embodiment the compound of formula (II) is N-{6-(cyclopropylamino)-9-[(1R,4S)-4-(hydroxymethyl) cyclopent-2-enyl]-9H-purin-2-yl}isobutyramide (compound of formula (II) where R=isopropyl).

Preferably, the base is an alkaline metal hydroxide such as lithium, sodium or potassium hydroxide. The most preferred alkaline metal hydroxide is sodium hydroxide. Preferably, the amount of inorganic base is comprised between 0.1 and 10 mol of base per mol of starting material of formula (II). More preferably, the amount of base is comprised between 1 and 5 mol of base per mol of starting material.

The hydrolysis is carried out in a mixture of water and an alcohol such as ethanol, n-propanol, isopropanol, n-butanol, isobutanol or t-butanol. Preferably, the solvent system is a mixture of isopropanol and water. Usually the amount of solvent is comprised between 1 and 15 ml/g of starting material. Preferably, between 2 and 10 ml/g. Likewise, the amount of water is usually comprised between 1-15 ml/g of starting material. Preferably between 1 and 10 ml/g.

The reaction is preferably carried out at a temperature comprised between room temperature and the reflux temperature of the solvent used. In a preferred embodiment, the reaction is carried out at a temperature comprised between 50° C. and the reflux temperature of the mixture. Thus, it is advantageous since surprisingly the reaction time is tremendously reduced at these temperatures while no significance by-products formation is observed. In a more preferred embodiment, the reaction is carried out at the reflux temperature of the mixture.

The abacavir can be isolated from the reaction medium as a pharmaceutically acceptable salt, preferably the hemisulfate salt, by separating the aqueous phase and precipitating the salt of abacavir from the organic phase by addition of the appropriate amount of the corresponding pharmaceutically acceptable acid. Optionally, a second solvent can be added before separation of the aqueous phase. Examples of suitable solvents include ($C_2$-$C_8$) aliphatic ethers such as ethyl ether, isopropyl ether, tert-butylmethyl ether, di-n-butyl ether or tetrahydrofuran, ($C_6$-$C_8$)-aromatic hydrocarbons such as toluene or xylene, or chlorine-containing solvents such as chloroform or methylene chloride. Optionally, the organic phase can be washed with aqueous sodium hydroxide or with an aqueous solution of another inorganic base before the addition of the pharmaceutically acceptable acid. Higher yields may be obtained when the salt of abacavir is isolated from a solvent in an anhydrous medium. For instance, the water can be removed by azeotropic distillation or by evaporation to dryness and then adding the appropriate solvent to precipitate the salt of abacavir.

The hemisulfate salt of {(1S,4R)-4-[2-amino-6-(cyclopropylamino)-9H-purin-9-yl]-cyclopent-2-enyl}methanol means the salt formed between {(1S,4R)-{4-[2-amino-6-(cyclopropylamino)-9H-purin-9-yl]-cyclopent-2-enyl}methanol and sulfuric acid in a stoichiometric ratio of 2:1.

Alternatively, abacavir can be isolated from the reaction medium as a free base by crystallization. A change of solvent may be carried out to perform the crystallization. Suitable crystallization solvent system is, for instance, ($C_2$-$C_6$)-alcohols such as ethanol, n-propanol, isopropanol, n-butanol, isobutanol or tert-butanol, ($C_3$-$C_9$)-ketones such as acetone, methylisobutylketone, or methylethylketone, ($C_2$-$C_8$) aliphatic ethers such as ethyl ether, isopropyl ether, tert-butylmethyl ether, di-n-butyl ether or tetrahydrofuran, ($C_2$-$C_{10}$)-esters such as ethyl acetate, acetonitrile, or mixtures thereof. Preferred solvent systems are acetone, acetonitrile, ethyl acetate, isopropanol or mixtures of isopropanol/tert-butyl methyl ether. Optionally, the organic phase can be washed with aqueous sodium hydroxide or with an aqueous solution of other inorganic base before crystallizing the abacavir as free base.

Abacavir can also be isolated from the reaction medium as a free base by optionally adding a solvent selected from ($C_2$-$C_8$)-aliphatic ethers and ($C_6$-$C_8$)-aromatic hydrocarbons, separating the aqueous phase, optionally removing the remaining water, and crystallyzing the abacavir of formula (I) as free base in an appropriate solvent system. Preferably, the crystallizing solvent system is selected from those mentioned above. Optionally, the organic phase can be washed with aqueous sodium hydroxide or with an aqueous solution of other inorganic base before crystallizing the abacavir as free base.

When a pharmaceutically acceptable salt is desired, it can also be obtained from the abacavir base by treatment with the corresponding acid. A preferred salt is the hemisulfate salt of abacavir.

The most adequate conditions for carrying out said process vary depending on the parameters considered by an expert in the art, such as, for example, the concentration of the reaction mixture, the temperature, the solvent used during the reaction and the isolation of the product, and the like. These can be readily determined by said skilled person in the art with the help of the teachings of the examples given in this description.

Throughout the description and claims the word "comprise" and variations of the word, are not intended to exclude other technical features, additives, components, or steps. The abstract of this application is incorporated herein as reference. Additional objects, advantages and features of the invention will become apparent to those skilled in the art upon examination of the description or may be learned by practice of the invention. The following examples are provided by way of illustration, and they are not intended to be limiting of the present invention.

EXAMPLES

Example 1

Preparation of Abacavir Hemisulfate

N-{6-(cyclopropylamino)-9-[(1R,4S)-4-(hydroxymethyl) cyclopent-2-enyl]-9H-purin-2-yl}isobutyramide (6.56 g, 18.40 mmol) was slurried in a mixture of isopropanol (32.8 ml) and 10% solution of NaOH (36.1 ml, 92.0 mmol). The mixture was refluxed for 1 h. The resulting solution was cooled to 20-25° C. and tert-butyl methyl ether (32.8 ml) was added. The layers were separated and H$_2$SO$_4$ 96% (0.61 ml, 11.03 mmol) was added dropwise to the organic layer. This mixture was cooled to 0-5° C. and the resulting slurry filtered off. The solid was dried under vacuum at 40° C. Abacavir hemisulfate (5.98 g, 97%) was obtained as a white powder.

Example 2

Preparation of Abacavir Hemisulfate

N-{6-(cyclopropylamino)-9-[(1R,4S)-4-(hydroxymethyl) cyclopent-2-enyl]-9H-purin-2-yl}isobutyramide (6.56 g, 18.40 mmol) was slurried in a mixture of isopropanol (32.8 ml) and 10% solution of NaOH (36.1 ml, 92.0 mmol). The mixture was refluxed for 1 h. The resulting solution was cooled to 20-25° C. and toluene (32.8 ml) was added. The layers were separated and H$_2$SO$_4$ 96% (0.61 ml, 11.03 mmol) was added dropwise to the organic layer. This mixture was cooled to 0-5° C. and the resulting slurry filtered off. The solid was dried under vacuum at 40° C. Abacavir hemisulfate (5.42 g, 88%) was obtained as a white powder.

Example 3

Preparation of Abacavir Hemisulfate

To a solution of N-{6-(cyclopropylamino)-9-[(1R,4S)-4-(hydroxymethyl) cyclopent-2-enyl]-9H-purin-2-yl}isobutyramide (1.0 g, 2.80 mmol) in isopropanol (10 ml) a 10% solution of NaOH (5.5 ml, 14.03 mmol) was added. The mixture was refluxed for 1 h. The resulting solution was cooled to 20-25° C. and the aqueous layer was separated. H$_2$SO$_4$ 96% (0.07 ml, 1.22 mmol) was added dropwise to the organic layer. The mixture was concentrated to half volume and the salts were filtered off. To the obtained solution, H$_2$SO$_4$ 96% (0.07 ml, 1.22 mmol) was added dropwise and cooled to 0-5° C. The solid was filtered off and dried under vacuum at 40° C. Abacavir hemisulfate (0.56 g, 60%) was obtained as a white powder.

Example 4

Preparation of Abacavir Hemisulfate

N-{6-(cyclopropylamino)-9-[(1R,4S)-4-(hydroxymethyl) cyclopent-2-enyl]-9H-purin-2-yl}isobutyramide (5.0 g, 14.03 mmol) was slurried in a mixture of isopropanol (25 ml) and 10% solution of NaOH (27.5 ml, 70.1 mmol). The mixture was refluxed for 1 h. The resulting solution was cooled to 20-25° C. and the aqueous solution was discarded. The organic layer was concentrated to dryness. isopropanol (10 ml) was added and further concentrated to dryness two times. To this residue, isopropanol (25 ml) was added and the salts were filtered off. To the obtained solution, H$_2$SO$_4$ 96% (0.39 ml, 7.0 mmol) was added dropwise. This mixture was cooled to 0-5° C. and the resulting slurry filtered off. The solid was dried under vacuum at 40° C. Abacavir hemisulfate (3.7 g, 79%) was obtained as a white powder.

Example 5

Preparation of Abacavir Hemisulfate

A mixture of N-{6-(cyclopropylamino)-9-[(1R,4S)-4-(hydroxymethyl)cyclopent-2-enyl]-9H-purin-2-yl}isobutyramide (10 g, 28 mmol), isopropanol (100 ml) and 10% solution of NaOH (16.8 ml, 42 mmol) was refluxed for 1 h. The resulting solution was cooled to 20-25° C. and washed several times with 25% solution of NaOH (10 ml). The wet organic layer was neutralized to pH 7.0-7.5 with 17% hydrochloric acid and it was concentrated to dryness under vacuum. The residue was taken in isopropanol (100 ml) and the salts were filtered off. To the filtrate, H$_2$SO$_4$ 96% (0.78 ml, 14.0 mmol) was added dropwise. This mixture was cooled to 0-5° C. and the precipitated was filtered and dried under vacuum at 40° C. to afford 15.0 g (80%) of abacavir hemisulfate as a white powder.

Example 6

Preparation of Abacavir

N-{6-(cyclopropylamino)-9-[(1R,4S)-4-(hydroxymethyl) cyclopent-2-enyl]-9H-purin-2-yl}isobutyramide (1.0 g, 2.80 mmol) was slurried in a mixture of isopropanol (2 ml) and 10% solution of NaOH (1.1 ml, 2.80 mmol). The mixture was refluxed for 1 h. The resulting solution was cooled to 20-25° C. and tert-butyl methyl ether (2 ml) was added. The aqueous layer was discarded, the organic phase was cooled to 0-5° C. and the resulting slurry filtered off. The solid was dried under vacuum at 40° C. Abacavir (0.62 g, 77%) was obtained as a white powder.

Example 7

Preparation of Abacavir

N-{6-(cyclopropylamino)-9-[(1R,4S)-4-(hydroxymethyl) cyclopent-2-enyl]-9H-purin-2-yl}isobutyramide (1.25 g, 3.51 mmol) was slurried in a mixture of isopropanol (2.5 ml) and 10% solution of NaOH (1.37 ml, 3.51 mmol). The mixture was refluxed for 1 h and concentrated to dryness. The residue was crystallized in acetone. Abacavir (0.47 g, 47%) was obtained as a white powder.

Example 8

Preparation of Abacavir

N-{6-(cyclopropylamino)-9-[(1R,4S)-4-(hydroxymethyl) cyclopent-2-enyl]-9H-purin-2-yl}isobutyramide (1.25 g, 3.51 mmol) was slurried in a mixture of isopropanol (2.5 ml) and 10% solution of NaOH (1.37 ml, 3.51 mmol). The mixture was refluxed for 1 h and concentrated to dryness. The residue was crystallized in acetonitrile. Abacavir (0.43 g, 43%) was obtained as a white powder.

Example 9

Preparation of Abacavir

A mixture of N-{6-(cyclopropylamino)-9-[(1R,4S)-4-(hydroxymethyl)cyclopent-2-enyl]-9H-purin-2-yl}isobutyramide (10 g, 28 mmol), isopropanol (100 ml) and 10% solution of NaOH (16.8 ml, 42 mmol) was refluxed for 1 h. The resulting solution was cooled to 20-25° C. and washed several times with 25% solution of NaOH (10 ml). The wet organic layer was neutralized to pH 7.0-7.5 with 17% hydrochloric acid and it was concentrated to dryness under vacuum. The residue was crystallized in ethyl acetate (150 ml) to afford abacavir (7.2 g, 90%).

Example 10

Preparation of Abacavir

A mixture of N-{6-(cyclopropylamino)-9-[(1R,4S)-4-(hydroxymethyl)cyclopent-2-enyl]-9H-purin-2-yl}isobutyramide (10 g, 28 mmol), isopropanol (100 ml) and 10% solution of NaOH (16.8 ml, 42 mmol) was refluxed for 1 h. The resulting solution was cooled to 20-25° C. and washed several times with 25% solution of NaOH (10 ml). The wet organic layer was neutralized to pH 7.0-7.5 with 17% hydrochloric acid and it was concentrated to dryness under vacuum. The residue was crystallized in acetone (300 ml) to afford abacavir (7.0 g, 88%).

The invention claimed is:

1. A process for the preparation of abacavir of formula (I), or a pharmaceutically acceptable salt thereof, comprising
   (a) reacting a compound of formula (II) with an inorganic base in a mixture of a $(C_1$-$C_6)$-alcohol and water, wherein R is H or a $(C_1$-$C_4)$-alkyl radical; and

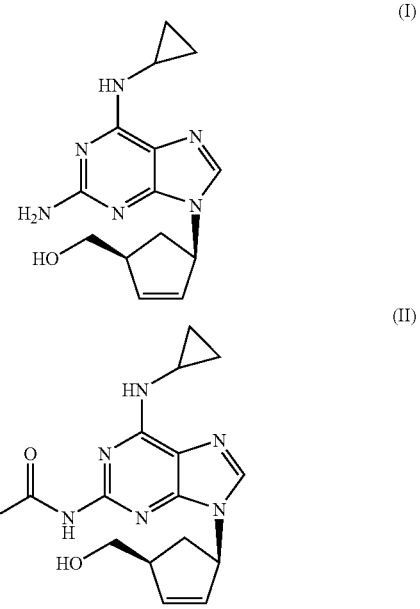

(b) isolating the abacavir of either as free base by crystallization or as a pharmaceutically acceptable salt by the alternative sequences,
   where for a salt:
      (b1) when at the end of reaction (a) the mixture is a solution, then, comprising:
         (i) adding a solvent selected from the group consisting of ethyl ether, isopropyl ether, tert-butylmethyl ether, di-n-butyl ether, (C6-C8)-aromatic hydrocarbons and chlorine-containing solvents;
         (ii) separating the aqueous phase; and
         (iii) precipitating the pharmaceutically acceptable salt from the organic phase by addition of the appropriate amount of the corresponding pharmaceutically acceptable acid; or
      (b2) when at the end of the reaction a separation of the mixture is observed in two phases as a two-phase system, then, comprising:
         (i) optionally adding to the two-phase system a solvent selected from the group consisting of ethyl ether, isopropyl ether, tert-butylmethyl ether, di-n-butyl ether, (C6-C8)-aromatic hydrocarbons and chlorine-containing solvents;
         (ii) separating the aqueous phase and
         (iii) precipitating the pharmaceutically acceptable salt of abacavir from the organic phase by addition of the appropriate amount of the corresponding pharmaceutically acceptable acid; or,
      where for a free base: alternatively isolating the abacavir as free base and converting the free base into a pharmaceutically acceptable salt by treating the free base with a suitable amount of the corresponding pharmaceutically acceptable acid.

2. The preparation process according to claim 1, wherein R is isopropyl.

3. The preparation process according to claim 1 wherein the inorganic base is an alkaline metal hydroxide.

4. The preparation process according to claim 3, wherein the alkaline metal hydroxide is sodium hydroxide.

5. The preparation process according to claim 1 wherein the (C1-C6)-alcohol is isopropanol.

6. The preparation process according to claim 1 wherein the reaction is carried out at a temperature of between 50° C. and the reflux temperature of the mixture.

7. The preparation process according to claim 1 wherein abacavir of formula (I) is isolated as a salt by the sequence of steps (b1) or (b2) for a salt, and the isolation process further comprises:
   carrying out at least one wash with an aqueous solution of an inorganic base; and
   optionally removing the remaining water; these steps being carried out after step (ii) and before
   precipitating the pharmaceutically acceptable salt.

8. The preparation process according to claim 7, wherein the salt of the abacavir of formula (I) is the hemisulfate salt.

9. The preparation process according to claim 1, wherein the abacavir of formula (I) is isolated as a free base and the isolation process comprises crystallizing the abacavir of formula (I) as a free base in an appropriate solvent system.

10. The preparation process according to claim 1, wherein the abacavir of formula (I) is isolated as a free base and the isolation process further comprises:
   (b1) when at the end of reaction (a) the mixture is a solution, then,
      (i) adding a solvent selected from the group consisting of ethyl ether, isopropyl ether, tert-butylmethyl ether, di-n-butyl ether and $(C_6$-$C_8)$-aromatic hydrocarbons;
      (ii) separating the aqueous phase;
      (iii) optionally, carrying out at least one wash with an aqueous solution of an inorganic base;
      (iv) optionally removing the remaining water;
      these steps being carried out before crystallizing the abacavir of formula (I) as free base in an appropriate solvent system; and if desired, treating the abacavir base crystallized with a pharmaceutically acceptable acid to form the corresponding salt;
   (b2) when at the end of the reaction a separation of the mixture is observed in two phases as a two-phase system, then,
      (i) optionally, adding to the two-phase system a solvent selected from the group consisting of ethyl ether, isopropyl ether, tert-butylmethyl ether, di-n-butyl ether, and $(C_6$-$C_8)$-aromatic hydrocarbons;
      (ii) separating the aqueous phase;
      (iii) optionally, carrying out at least one wash of the organic phase with an aqueous solution of an inorganic base;
      (iv) optionally, removing the remaining water;

these steps being carried out before crystallizing the abacavir of formula (I) as free base in an appropriate solvent system; and if desired, treating the abacavir base crystallized with a pharmaceutically acceptable acid to form the corresponding salt.

11. The preparation process according to claim 9, wherein the appropriate solvent system for crystallization of the free base of the abacavir is selected from the group consisting of acetone, acetonitrile, ethyl acetate, isopropanol and mixtures of isopropanol/tert-butyl methyl ether.

12. The preparation process according to claim 2, wherein the inorganic base is sodium hydroxide.

13. The preparation process according to claim 12, wherein the abacavir of formula (I) is isolated as a salt by the sequence of steps (b1) or (b2) for a salt and the isolation process further comprises:
 carrying out at least one wash with an aqueous solution of an inorganic base;
 optionally removing the remaining water;
 these steps being carried out after step (II) and before precipitating the pharmaceutically acceptable salt.

14. The preparation process according to claim 12, wherein the abacavir of formula (I) is isolated as a free base and the isolation process comprises crystallizing the abacavir of formula (I) as a free base in an appropriate solvent system.

15. The preparation process according to claim 12, wherein the abacavir of formula (I) is isolated as a free base and the isolation process further comprises:
 (b1) when at the end of reaction (a) the mixture is a solution, then,
  (i) optionally adding a solvent selected from the group consisting of ethyl ether, isopropyl ether, tert-butylmethyl ether, di-n-butyl ether and ($C_6$-$C_8$)-aromatic hydrocarbons;
  (ii) separating the aqueous phase;
  (iii) optionally, carrying out at least one wash with an aqueous solution of an inorganic base;
  (iv) optionally removing the remaining water;
  these steps being carried out before crystallyzing the abacavir (I) as free base in an appropriate solvent system; and if desired, treating the abacavir base crystallized with a pharmaceutically acceptable acid to form the corresponding salt;
 (b2) when at the end of the reaction a separation of the mixture is observed in two phases as a two-phase system, then,
  (i) optionally, adding to the two-phase system a solvent selected from the group consisting of ethyl ether, isopropyl ether, tert-butylmethyl ether, di-n-butyl ether, and ($C_6$-$C_8$)-aromatic hydrocarbons;
  (ii) separating the aqueous phase;
  (iii) optionally, carrying out at least one wash with an aqueous solution of an inorganic base;
  (iv) optionally removing the remaining water;
  these steps being carried out before crystallizing the abacavir of formula (I) as free base in an appropriate solvent system; and if desired, treating the abacavir base crystallized with a pharmaceutically acceptable acid to form the corresponding salt.

16. The preparation process according to claim 10, wherein the solvent system for crystallization of the free base of the abacavir of formula (I) is selected from the group consisting of acetone, acetonitrile, ethyl acetate, isopropanol and mixtures of isopropanol/tert-butyl methyl ether.

17. The preparation process according to claim 2, wherein the base is sodium hydroxide and the alcohol is isopropanol.

18. The preparation process according to claim 9, further comprising treating the compound obtained with a pharmaceutically acceptable acid to form the corresponding salt.

19. The preparation process according to claim 14, further comprising treating the compound obtained with a pharmaceutically acceptable acid to form the corresponding salt.

* * * * *